United States Patent [19]
Tan et al.

[11] Patent Number: 5,916,670
[45] Date of Patent: Jun. 29, 1999

[54] ABSORBENT MATERIAL FOR USE IN ABSORBENT ARTICLES

[75] Inventors: Erol Tan; Peter R. Abitz, both of St. Simmons Island; Kays Chinai, St. Simmons Island, all of Ga.

[73] Assignee: Rayonier Inc., Stanford, Conn.

[21] Appl. No.: 08/948,987

[22] Filed: Oct. 10, 1997

Related U.S. Application Data

[63] Continuation-in-part of application No. 08/784,536, Jan. 17, 1997.

[51] Int. Cl.$^6$ ..................................................... D21H 13/02
[52] U.S. Cl. .......................... 428/219; 428/124; 428/913; 442/412; 442/413; 442/417; 162/146; 162/157.6; 162/164.1
[58] Field of Search ..................................... 428/124, 219, 428/913; 442/412, 413, 417; 162/146, 157.6, 164.1

[56] References Cited

U.S. PATENT DOCUMENTS

| | | |
|---|---|---|
| 4,610,678 | 9/1986 | Weisman et al. . |
| 5,516,569 | 5/1996 | Veith et al. . |
| 5,547,541 | 8/1996 | Hansen et al. . |
| 5,562,645 | 10/1996 | Tanzer et al. . |
| 5,635,239 | 6/1997 | Chen et al. . |

FOREIGN PATENT DOCUMENTS 0 763 364 A2  3/1997  European Pat. Off. .

*Primary Examiner*—Christopher Raimund
*Attorney, Agent, or Firm*—Rockey, Milnamow & Katz, Ltd.

[57] ABSTRACT

An absorbent material that can be used as an absorbent core in absorbent articles such as disposable diapers, feminine hygiene products and incontinence devices is provided. An absorbent material of this invention contains cellulosic fibers at least a portion of which cellulosic fibers are treated with caustic at a low temperature. The absorbent material has superior absorptive, strength, and suppleness properties when compared to existing core materials. The material can be air-laid in one or more layers.

50 Claims, 7 Drawing Sheets

FIG. 2
Feminine Hygiene Products:
Total Basis Weight $\cong$ 200 g/cm$^2$
Three Strata
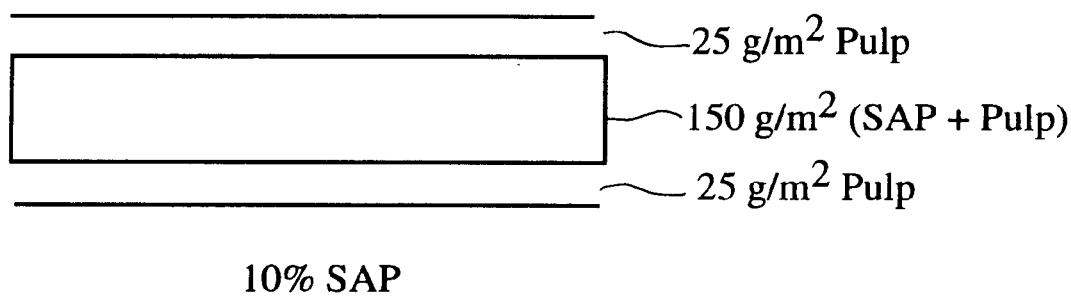
- 25 g/m$^2$ Pulp
- 150 g/m$^2$ (SAP + Pulp)
- 25 g/m$^2$ Pulp
10% SAP
Four Strata
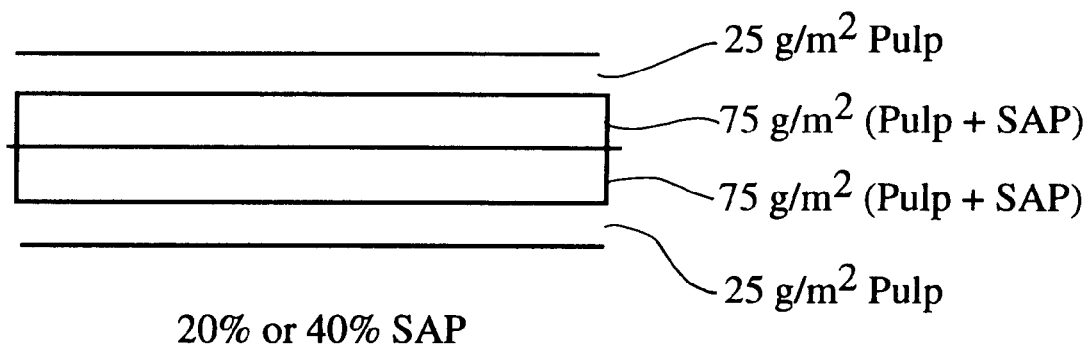
- 25 g/m$^2$ Pulp
- 75 g/m$^2$ (Pulp + SAP)
- 75 g/m$^2$ (Pulp + SAP)
- 25 g/m$^2$ Pulp
20% or 40% SAP

FIG. 3
Diapers and Incontinence Products:
Total Weight ≅ 400 g/cm$^2$
Three Strata
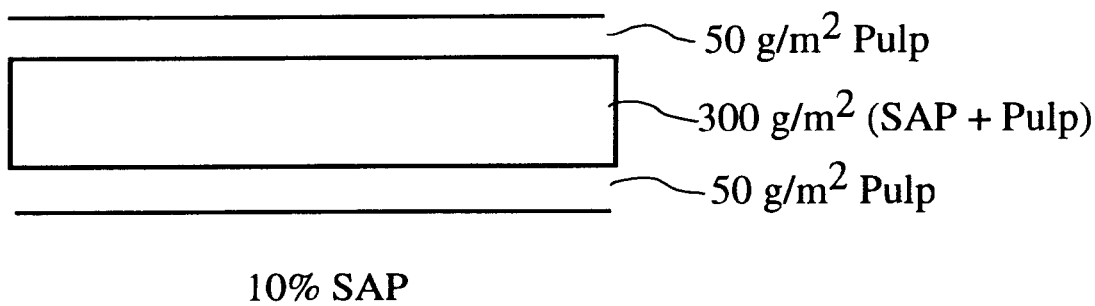
- 50 g/m$^2$ Pulp
- 300 g/m$^2$ (SAP + Pulp)
- 50 g/m$^2$ Pulp
10% SAP
Four Strata
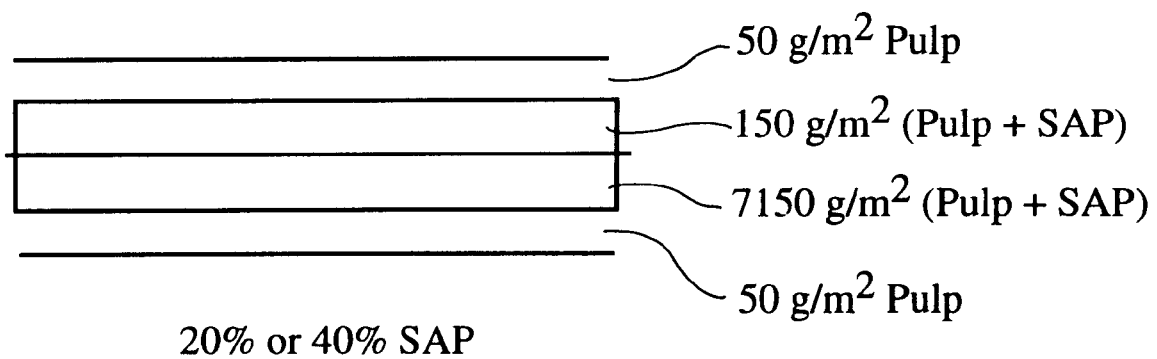
- 50 g/m$^2$ Pulp
- 150 g/m$^2$ (Pulp + SAP)
- 7150 g/m$^2$ (Pulp + SAP)
- 50 g/m$^2$ Pulp
20% or 40% SAP 45° Wicking Energy

DRYING POWER INSTRUMENT

TEST ASSEMBLY

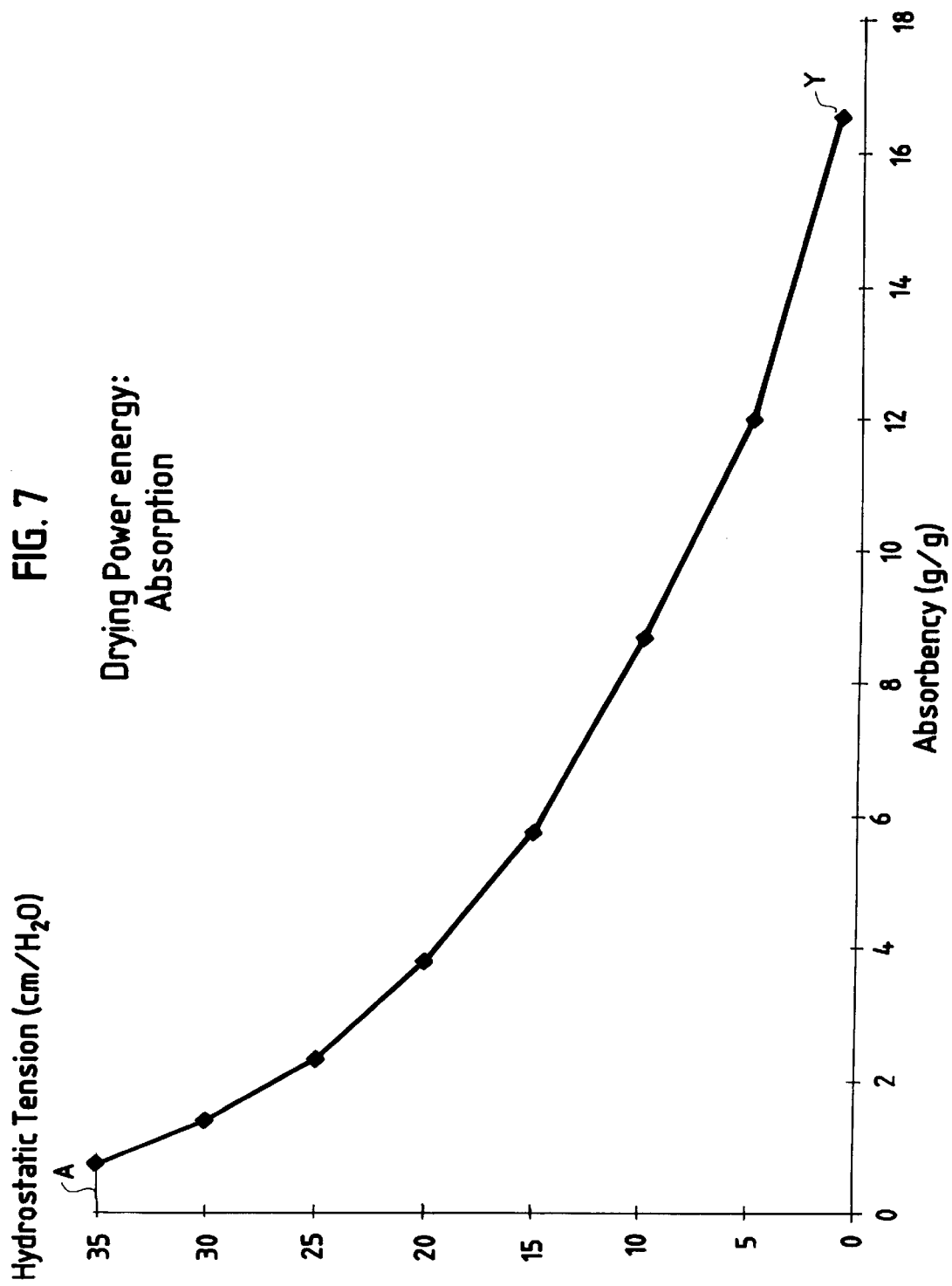

ABSORBENT MATERIAL FOR USE IN ABSORBENT ARTICLES

CROSS-REFERENCE TO RELATED APPLICATION

This application is a continuation-in-part application of U.S. patent application Ser. No. 08/784,536 filed Jan. 17, 1997, now pending, the disclosure of which is incorporated herein by reference.

TECHNICAL FIELD OF THE INVENTION

This invention relates to absorbent materials to be used as absorbent cores in articles such as disposable diapers, feminine hygiene products and incontinence devices. More particularly, the present invention relates to absorbent materials that are high density, strong, soft materials with superior absorption properties.

BACKGROUND OF THE INVENTION

Disposable absorbent articles, such as diapers, feminine hygiene products, adult incontinence devices and the like have found widespread acceptance. To function efficiently, such absorbent articles must quickly absorb body fluids, distribute those fluids within and throughout the absorbent article and be capable of retaining those body fluids with sufficient energy to dry the surface when placed under loads. In addition, the absorbent article need be sufficiently soft and flexible so as to comfortably conform to body surfaces and provide close fit for lower leakage.

While the design of individual absorbent articles varies depending upon use, there are certain elements or components common to such articles. The absorbent article contains a liquid pervious top sheet or facing layer, which facing layer is designed to be in contact with a body surface. The facing layer is made of a material that allows for the unimpeded transfer of fluid from the body into the core of the article. The facing layer should not absorb fluid per se and, thus, should remain dry. The article further contains a liquid impervious back sheet or backing layer disposed on the outer surface of the article and which layer is designed to prevent the leakage of fluid out of the article.

Disposed between the facing layer and backing layer is an absorbent member referred to in the art as an absorbent core. The function of the absorbent core is to absorb and retain body fluids entering the absorbent article through the facing layer. Because the origin of body fluids is localized, it is necessary to provide a means for distributing fluid throughout the dimensions of the absorbent core to make full use of all the available absorbent material. This is typically accomplished either by providing a distribution member disposed between the facing layer and absorbent core and/or altering the composition of the absorbent core per se.

Fluid can be distributed to different portions of the absorbent core by means of a transfer or acquisition layer disposed between the facing layer and core. Because of the proximity of such an acquisition layer to the body surface of the wearer, the acquisition layer should not be formed from material that retains large amounts of fluid. The purpose of the acquisition layer is to provide for rapid transfer and distribution of fluid to the absorbent core while minimizing spread of the fluid in this layer.

The absorbent core is typically formulated of a cellulosic wood fiber matrix or pulp, which pulp is capable of absorbing large quantities of fluid. Absorbent cores can be designed in a variety of ways to enhance fluid absorption and retention properties. By way of example, the fluid retention characteristics of absorbent cores can be greatly enhanced by disposing superabsorbent materials in amongst fibers of the wood pulp. Superabsorbent materials are well known in the art as substantially water-insoluble, absorbent polymeric compositions that are capable of absorbing large amounts of fluid in relation to their weight and forming hydrogels upon such absorption. Absorbent articles containing blends or mixtures of pulp and superabsorbents are known in the art.

The distribution of superabsorbents within an absorbent core can be uniform or non-uniform. By way of example, that portion of an absorbent core proximate to the backing layer (farthest away from the wearer) can be formulated to contain higher levels of superabsorbent than those portions of the core proximate the facing or acquisition layer. By way of further example, that portion of the core closest to the site of fluid entry (e.g., acquisition zone) can be formulated to transport (wick) fluid into surrounding portions of the core (e.g., storage zone).

In addition to blending pulp with superabsorbent material, a variety of other means for improving the characteristics of pulp have been described. For example, pulp boards can be more easily defiberized by using chemical debonding agents (see, e.g., U.S. Pat. No. 3,930,933). In addition, cellulose fibers of wood pulp can be flash-dried prior to incorporation into a composite web absorbent material (see, e.g., U.K. Patent Application GB 2272916A published on Jun. 1, 1994). Still further, the individualized cellulosic fibers of wood pulp can be cross-linked (see, e.g., U.S. Pat. Nos. 4,822,453; 4,888,093; 5,190,563; and 5,252,275). All of these expedients have the disadvantage of requiring the wood pulp manufacturer to perform time-intensive, expensive procedures during the wood pulp preparation steps. Thus, use of these steps results in substantial increases in the cost of wood pulp.

Although all of the above treatment steps have been reported to improve the absorption characteristics of pulp for use as absorbent cores, there are certain disadvantages associated with such treatments. By way of example, the manufacturer of the end use absorbent article (e.g. feminine hygiene product or diaper) must fluff the fibers in the wood pulp so as to detach the individual fibers bound in that pulp. Typically, pulp has a low moisture content, which results in the individual fibers being relatively brittle resulting in fine dust due to fiber breakage during fluffing operation. If the pulp manufacturer performs such fluffing prior to shipment to the absorbent article maker, the transportation costs of the pulp are increased. At least one pulp manufacturer has attempted to solve this problem by producing flash-dried pulp without chemical bonding agents in a narrow range of basis weights in pulp density (see U.S. Pat. No. 5,262,005). However, even with this process, the manufacturer of the absorbent article must still process the pulp after purchase.

There have been numerous attempts by the manufacturers of absorbent materials to produce highly absorbent, strong, soft core materials. U.S. Pat. No. 4,610,678 discloses an air-laid material containing hydrophilic fibers and superabsorbent material, wherein the material is air-laid in a dry state and compacted without the use of any added binding agents. Such material, however, has low integrity and suffers from shake-out or loss of substantial amounts of superabsorbent material. U.S. Pat. No. 5,516,569 discloses that superabsorbent material shake-out can be reduced in air-laid absorbents by adding significant amounts of water to material during the air-laying process. The resultant material, however, is stiff, of low density and has a high water content (>about 15 weight percent). The high stiffness can be reduced using embossing. U.S. Pat. No. 5,547,541 discloses that high density air-laid materials containing hydrophilic fibers and superabsorbent material can be made by adding densifying agents to the material. The use of such agents, however, increases the production cost of the material.

U.S. Pat. No. 5,562,645 discloses low density (density less than 0.25 g/cc) absorbent materials. The use of such low density, bulky materials increases the cost of transportation and handling. U.S. Pat. No. 5,635,239 discloses an absorbent material that contains two complex forming agents that interact when wetted to form a complex. The complex forming agents are polymeric olefins. European Patent Application No. EP 0763364 A2 discloses absorbent material that contains cationic and anionic binders that serve to hold the superabsorbent material within the material. The use of such agents and binders increase the cost of making the absorbent material and pose a potential environmental hazard.

There continues to be a need in the art, therefore, for a material that satisfies the absorbency, strength and softness requirements needed for use as absorbent core in disposable absorbent articles and which simultaneously provides time and cost savings to both the pulp manufacturer and the manufacturer of the absorbent article.

BRIEF SUMMARY OF THE INVENTION

In one aspect, the present invention provides an absorbent material having a basis weight of from about 100 g/m$^2$ to about 500 g/m$^2$, a density of from about 0.25 g/cc to about 0.50 g/cc, the material including a core having cellulosic fibers and a layer of tissue superimposed on an outer surface of the core, wherein at least some of the cellulosic fibers have been made by a process that includes the step of treating a liquid suspension of pulp at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes. Preferably, the material has a basis weight of from about 100 g/m$^2$ to about 250 g/m$^2$ or a basis weight of from about 350 g/m$^2$ to about 450 g/m$^2$ and a density of from about 0.30 to about 0.45 g/cc.

Preferably, at least about 25 percent, 40 percent or 50 percent of the fibers are made by the process. The absorbent material can contain from about 40 weight percent to about 100 weight percent cellulosic fibers and from about 0 weight percent to about 60 weight percent superabsorbent material. Preferably, the material contains from about 10 to about 60 weight percent superabsorbent material and, more preferably from about 20 to about 40 weight percent superabsorbent material.

The material of the present invention has superior absorptive properties. The material has a normalized drying power energy of at least 6,000 ergs/g. Preferably, the normalized drying power energy of the material is greater than about 7,000, 8,000, 9,000 or 10,000 ergs/g. More preferably, the normalized drying power is between about 6,000 ergs/g and about 16,000 ergs/g. The material has a normalized wicking energy of at least 3,000 ergs/g. Preferably, the normalized wicking energy is greater than about 3,500, 4,000, 5,000, or 7,500 ergs/g. More preferably, the normalized wicking energy is between about 3,000 ergs/g and about 10,000 ergs/g. In an especially preferred embodiment, the material of this invention has a normalized drying power energy of at least 6,000 ergs/g and a wicking energy of at least about 3,000 ergs/g.

An absorbent material of the present invention is supple. The suppleness, defined as the inverse of stiffness, is greater than about 0.7 g$^{-1}$. Preferably, the suppleness is greater than about 0.8, 0.9, or 1.0 g$^{-1}$.

The absorbent material most preferably has a suppleness of greater than about 0.7 g$^{-1}$, a normalized drying power energy of greater than about 6,000 ergs/g and a normalized wicking energy greater than about 3,000 ergs/g.

In another aspect, the present invention provides an absorbent material having a density of from about 0.25 to about 0.5 g/cc and a suppleness of greater than about 0.7 g$^{-1}$, wherein the material consists essentially of: (a) from about 40 weight percent to about 90 weight percent cellulosic fibers at least some of which fibers have been made by a process that includes the step of treating a liquid suspension of pulp at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes; and (b) from about 10 weight percent to about 60 weight percent superabsorbent polymer. The material can further comprise a layer of tissue comprising from about 3 weight percent to about 20 weight percent of the absorbent material. Preferably, such a material has a density of from about 0.30 to about 0.45 g/cc, a suppleness of greater than about 0.7 g$^{-1}$, a normalized drying power energy of greater than about 6,000 ergs/g and a normalized wicking energy of greater than about 3,000 ergs/g. An especially preferred absorbent material of this invention has a density of from about 0.35 g/cc to about 0.45 g/cc, a basis weight of from about 200 g/m$^2$ to about 500 g/m$^2$, a suppleness of greater than about 0.9 g$^{-1}$, a normalized drying power energy of greater than about 6,000 ergs/g and a normalized wicking energy greater than about 3,000 ergs/g. That material consists essentially of: (a) from about 60 weight percent to about 80 weight percent cellulosic fibers at least some of which fibers have been made by a process that includes the step of treating a liquid suspension of pulp at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes; and (b) from about 20 weight percent to about 40 weight percent superabsorbent material; and (c) a layer of tissue comprising from about 3 weight percent to about 20 weight percent of the absorbent material.

The present invention still further provides absorbent articles that include an absorbent material of this invention. Preferably, the absorbent article is a diaper, a feminine hygiene product or an incontinence device.

BRIEF DESCRIPTIONS OF THE DRAWINGS

In the drawings, which form a portion of the specification:

FIG. 2 shows a three and four strata embodiments of an absorbent material of the present invention for use in a diaper or incontinence device.

FIG. 3 shows three and four strata embodiments of an absorbent material of the present invention for use as an absorbent core in a feminine hygiene product.

FIG. 7 is a representative plot of fluid absorption versus hydrostatic pressure obtained in a drying power test.

DETAILED DESCRIPTION OF THE INVENTION

Figure 1:
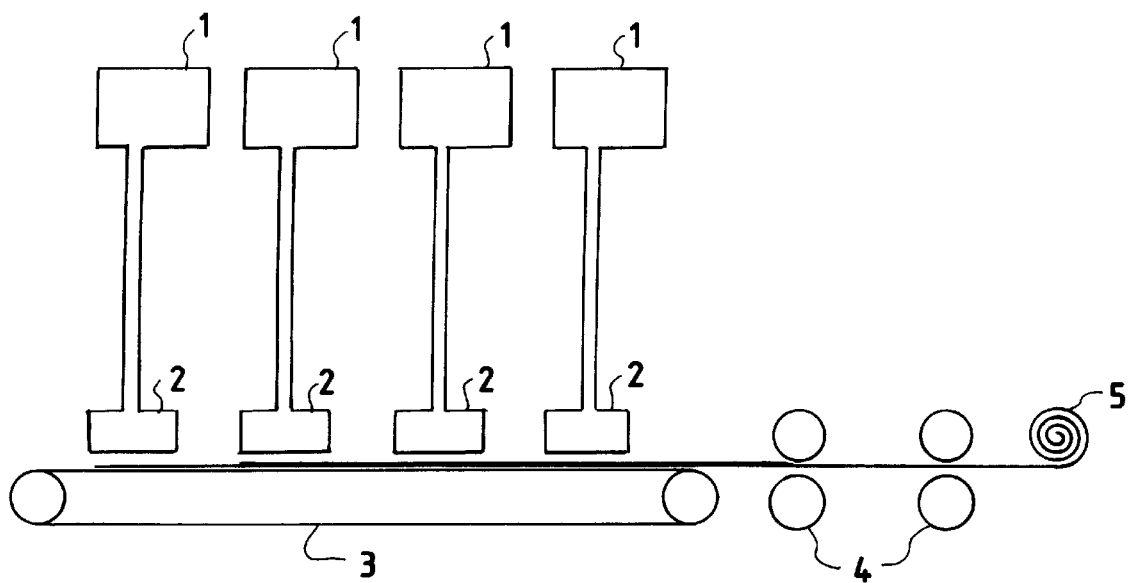
FIG. 1 is a schematic illustration of means for air-laying absorbent material of the present invention using four air-laying heads followed by means for compacting the air-laid material.

The present invention provides novel, absorbent material that is particularly well suited for use as cores in absorbent articles such as diapers, feminine hygiene products, incontinence devices and the like. The material of the present invention is a blend or mixture of cellulosic fibers and superabsorbent disposed in and amongst fibers of that pulp. A material of this invention has a unique combination of suppleness, strength and absorbency characteristics that make it particularly suitable for use in absorbent articles. An absorbent material of the present invention can be used directly by a manufacturer of the absorbent article without the need for any additional processing by that manufacturer other than cutting to the desired size and shape for the absorbent article.

The present invention relates to an absorbent material containing cellulosic fibers and superabsorbent material, which material is soft, thin, and of high density. Additionally, the material has enhanced absorption properties and firmly entraps superabsorbent material in the fiber network without the use of water, chemicals, binders, adhesives, thermoplastic resins, thermoplastic binder fibers, complex forming materials or the like. The absorbent has enough integrity (strength) to be processed on conventional disposable product manufacturing equipment without fiber breakage.

In one aspect, the present invention provides an absorbent material that contains from about 40 weight percent to about 100 weight percent cellulosic fibers and from about 0 weight percent to about 60 weight percent superabsorbent material. The absorbent material has a water content of less than about 10 weight percent. As used herein, the phrase "weight percent" means weight of substance per weight of final material as determined under ambient conditions. By way of example, 10 weight percent superabsorbent material means 10 $g/m^2$ superabsorbent material per 100 $g/m^2$ basis weight of the absorbent material.

Cellulosic fibers that can be used in a material of the present invention are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

As set forth above, a preferred cellulosic fiber for use in the present material is wood pulp. There are certain characteristics of wood pulp that make it particularly suitable for use. Cellulose in most wood pulps has a crystalline form known as Cellulose I, which can be converted to a form known as Cellulose II. In the present material, wood pulp with a substantial portion of the cellulose as Cellulose II is preferred. Similarly, pulps having an increase fiber curl value are preferred. Finally, pulps having reduced levels of hemicellulose are preferred. Means for treating pulps so as to optimize these characteristics are well known in the art.

By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus, it is preferred that the cellulosic fibers used to produce the material of this invention contain at least a portion of cold caustic treated pulp.

A description of the cold caustic extraction process can be found in U.S. patent application Ser. No. 08/370,571, now pending, filed on Jan. 18, 1995, which application is a continuation-in-part application of U.S. patent application Ser. No. 08/184,377, now abandoned, filed on Jan. 21, 1994. The disclosures of both of these applications are incorporated in their entirety herein by reference.

Briefly, a caustic treatment is typically carried out at a temperature less than about 60° C., but preferably at a temperature less than 50° C., and more preferably at a temperature between about 10° C. to 40° C. A preferred alkali metal salt solution is a sodium hydroxide solution newly made up or as a solution by-product in a pulp or paper mill operation, e.g., hemicaustic white liquor, oxidized white liquor and the like. Other alkali metals such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

An absorbent material of the present invention can contain any superabsorbent material, which superabsorbent materials are well known in the art. As used herein, the term "superabsorbent material" means a substantially water-insoluble polymeric material capable of absorbing large quantities of fluid in relation to their weight. The superabsorbent material can be in the form of particulate matter, flakes, fibers and the like. Exemplary particulate forms include granules, pulverized particles, spheres, aggregates and agglomerates. Exemplary and preferred superabsorbent materials include salts of crosslinked polyacrylic acid such as sodium polyacrylate. Superabsorbent materials are commercially available (e.g., Stockhausen GmbH, Krefeld, Germany).

In accordance with a preferred embodiment, the material contains from about 40 to about 100 weight percent cellulosic fibers and, more preferably from about 60 to about 80 weight percent cellulosic fibers. Such a material preferably contains from about 0 to about 60 weight percent superabsorbent material and, more preferably from about 20 to about 40 weight percent superabsorbent material.

An absorbent material is made using air-laying means well known in the art (See FIG. 1). In accordance with FIG. 1, cellulosic fibers (e.g., pulp) are processed using a hammer mill to individualize the fibers. The individualized fibers are blended with superabsorbent material granules in a blending system 1 and pneumatically conveyed into a series of forming heads 2. The blending and distribution of absorbent materials can be controlled separately for each forming head. Controlled air circulation and winged agitators in each chamber produce uniform mixture and distribution of pulp and superabsorbent material. The superabsorbent material can be thoroughly and homogeneously blended throughout the web or contained only in specific strata by distributing it to selected forming heads. Fibers (and superabsorbent material) from each forming chamber are deposited by vacuum onto a forming wire 3 thus forming a layered absorbent web. The web is subsequently compressed using heated calendars 4 to achieve desirable density. The densified web is wound into a roll 5 using conventional winding equipment. The forming wire 3 is covered with tissue to reduce the loss of material. The tissue layer is preferably incorporated into the formed material.

Means for selecting a suitable tissue for use in an absorbent material are well known to one of skill in the art. Exemplary and preferred such tissue is made of bleached wood pulp and has an air permeability of about 273–300 CFM (cubic feet minute). The tensile strength of the tissue is such that it retains integrity during formation and calendering of the absorbent material. Suitable MD and CD tensile strengths, expressed in Newtons/meter, are about 100–130 and 40–60, respectively. Tissue for use in air-laying absorbent materials are commercially available (e.g., Duni AB, Sweden).

An absorbent material of the present invention is of high density and has a density of greater than about 0.25 g/cc. In preferred embodiments, the material has density in the range of from about 0.25 g/cc to about 0.50 g/cc. More preferably, the density is from about 0.30 g/cc to about 0.45 g/cc. Most preferably, the density is from about 0.35 g/cc to about 0.45 g/cc.

Air-laid absorbents are typically produced with a low density. To achieve higher density levels, such as preferred in the material of the present invention, the air-laid material is compacted using calendars as shown in FIG. 1. Compaction is accomplished using means well known in the art. Typically such compaction is carried out at a temperature of about 100° C. and a pressure of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be shallow engraved. As set forth hereinafter in the Examples, use of engraved upper roll may result in formation of a material having slower fluid absorption rates. The preference for calendering with smooth rolls is surprising in light of the teaching of U.S. Pat. No. 5,516,569, which teaches that such calendering results in increased Gurley stiffness and damage to the absorbent material.

A high density absorbent material of the present invention that contains superabsorbent material is surprisingly and unexpectedly supple. Such material has a ratio of Gurley stiffness, measured in milligrams (mg) to density, measured in grams per cubic centimeter (g/cc), of less than about 4000. In preferred embodiments, that ratio of Gurley stiffness to density is less than about 3200 and, more preferably, less than about 3000.

Gurley stiffness measures the stiffness of absorbent materials. The greater the value of Gurley stiffness, the more rigid and inflexible the material. The inverse of Gurley stiffness, expressed as inverse grams ($g^{-1}$), is thus a measure of the softness, bendability and flexibility of absorbent materials. The term "suppleness" is used herein to describe these characteristics of softness, flexibility and bendability. Suppleness is defined and expressed as the inverse of Gurley stiffness and has the units $g^{-1}$.

As set forth hereinafter in the examples, suppleness was determined on absorbent material of the present invention as well as absorbent core material from two commercially available disposable diapers. The suppleness was determined at a number of different densities. The material of the present invention was substantially and significantly more supple than existing, commercially available material at every density tested. The material of the present invention has a suppleness of at least 0.7 $g^{-1}$. Preferably, the suppleness is greater than 0.8, 0.9, or 1.0 $g^{-1}$.

An absorbent material of the present invention is strong in light of its suppleness. Pad integrity is a well known measurement of absorbent material strength. A material of the present invention demonstrates strength (high pad integrity) over a wide range of densities (See the Examples hereinafter). For any given density within the range of 0.25 to 0.50 g/cc, material of the present invention has significantly greater (about 2 to 3 times) pad integrity than does the tested commercially available materials.

An absorbent material of this invention can be prepared over a wide range of basis weights without adversely affecting its softness or strength. Thus, the material can have a basis weight in the range of from about 50 $g/m^2$ to about 700 $g/m^2$. In a preferred embodiment, the basis weight ranges from about 100 $g/m^2$ to about 500 $g/m^2$ and, more preferably from about 100 $g/m^2$ to about 250 $g/m^2$ or from about 350 $g/m^2$ to about 450 $g/m^2$.

In addition to being supple and strong, an absorbent material of the present invention has superior absorptive properties when compared to existing materials. The absorptive properties of materials can be evaluated in a variety of ways. Of particular relevance to manufacturers of absorbent articles is the ability of the material to absorb large quantities of fluid against a load and to distribute that fluid away from the point of fluid entry.

Wicking is the ability of an absorbent material to direct fluid away from the point of fluid entry and distribute that fluid throughout the material. An absorbent material of this invention has surprisingly superior wicking properties when compared to absorbent cores from commercially available absorbent articles (e.g., Huggies or Pampers diapers). As described in detail hereinafter in the Examples, the wicking properties of two embodiments of a present invention wicked substantial amounts of fluid over 6 inches from the point of fluid entry. In a 400 $g/m^2$ basis weight, 20 weight percent superabsorbent material, the 45 wicking distribution at 5 inches was about 8 grams of fluid per gram of material. That same material had a wicking distribution at 7 inches of about 1.7 grams of fluid. Similar wicking properties were seen in a 600 $g/m^2$ basis weight, 40 weight percent absorbent material of the present invention. In contrast, the absorbent core from a Huggies or Pampers diaper, had a wicking distribution at 6 inches of less than 1 gram of fluid per gram of material. Neither commercially available diaper core distributed any substantial amounts of fluid beyond 6 inches.

The wicking capability of an absorbent material can be better characterized by expressing the wicking properties over the entire length of a tested sample. As set forth in detail hereinafter in the Examples, by calculating the total amount of fluid absorbed and wicked by a test sample (calculating the areas under a plot of absorbed fluid vs distance), a wicking energy (the capacity of the absorbent material to perform absorptive work) can be calculated. Because absorption is a function of superabsorbent material content, that energy can be normalized for superabsorbent material content. The resulting value is referred to herein as "normalized wicking energy" and has the units ergs/g. As set forth in detail hereinafter in Example 6, the normalized wicking energy was determined for absorptive material of the present invention as well as commercially available absorptive material. The data show that an absorptive material of the present invention has a normalized wicking energy of at least about 3,000 ergs/g. More preferably, the normalized wicking energy is greater than about 3,500, 4,000, 5,000, or 7,500 ergs/g. Most preferably, the absorptive material of the present invention has a normalized wicking energy of from about 3,000 to about 10,000 ergs/g. These values can be seen to be significantly greater than the values obtained from other materials.

It is important that an absorbent material designed for use in articles such as diapers, feminine hygiene products and incontinence devices be able to absorb fluid against a hydrostatic pressure gradient. One measure of such an absorptive capacity is drying power, which measures the absorption of fluid against a negative hydrostatic pressure applied to the fluid source. The drying power test is described generally in Burgeni et al., *Textile Research Journal,* 37:362, 1967 and, in detail, hereinafter in Example 7. As was the case for wicking energy, by calculating the total amount of fluid absorbed during the drying power test (calculating the area under a plot of absorbed fluid vs pressure), the work performed by the tested material can be calculated. As used herein, the phrase "drying power energy" refers to such drying power work. The units of drying power energy are ergs/g. Drying power energy corrected for superabsorbent material content is referred to herein as "normalized drying power energy".

Normalized drying power energy was determined for absorptive material of the present invention as well a number of commercially available materials. The data show that the absorptive material of this invention has a normalized drying power energy of at least 6,000 ergs/g. Preferably, the normalized drying power energy is greater than about 7,000, 8,000, 9,000 or 10,000 ergs/g. Most preferably, material of the present invention has a normalized drying power energy of from about 6,000 to about 16,000 ergs/g.

The unique combination of strength, absorptive ability and suppleness seen in the present absorbent material has significant advantages to a manufacturer of absorbent articles. Typically such a manufacturer purchases pulp and has to process that pulp on-line in their manufacturing plant as the final article (e.g., diaper, sanitary napkin) is being made. Such processing steps may include defibering of the pulp, adding superabsorbent and the like. In an on-line system, the rapidity with which such steps can be carried out is limited by the slowest of the various steps. An example of a pulp that requires such processing steps (e.g., defibering) is disclosed in U.S. Pat. No. 5,262,005.

The need of the manufacturer to defiberize or otherwise process existing materials on-line means that the overall production process is substantially more complex. Further, the manufacturer must purchase, maintain and operate the equipment needed to carry out such processing steps. The overall production cost is thus increased.

An absorbent material of the present invention can be directly incorporated into a desired absorbent article without the need for such processing steps. The manufacturer of the absorbent article does not have to defiber or otherwise treat the materials of the present invention in any way other than shaping the material into the desired shape. In this way, the manufacturer can speed up the assembly process and realize substantial savings in cost and time.

The material of this invention can be formed as a single blend of cellulosic fibers and superabsorbent material or air-laid as a plurality of layers or strata. In one embodiment, the material is formed as a single layer containing both cellulosic fibers and superabsorbent material. In another embodiment, the material is formed as two layers. Each of the layers can contain cellulosic fibers and superabsorbent material although it is possible to limit the superabsorbent material to only one layer. A preferred material of the present invention is air-laid as three or four lamina or strata. Those strata include a bottom layer, one or two middle layers and a top layer. Preferred embodiments of three and four layer material are set forth below. The superabsorbent material can be included in any or all of the layers. The concentration (weight percent) of superabsorbent material in each layer can vary as can the nature of the particular superabsorbent material. Five or more layer material is also contemplated by this invention.

An unexpected characteristic of the material of this invention is its ability to retain superabsorbent material when subjected to mechanical stress. In contrast to conventionally formed core materials, the material of the present invention retained over 85 percent by weight of its superabsorbent material content when subjected to 10 minutes of rigorous shaking (See, e.g., Example 4). Preferably, a material of this invention retains over 90 percent, preferably over 95 percent and, more preferably over 99 percent of its superabsorbent material under these mechanical stresses.

Even where prepared as from multiple layers, the final thickness of the formed material is low. The thickness can vary from about 0.5 mm to about 2.5 mm. In a preferred embodiment, the thickness is from about 1.0 mm to about 2.0 mm and, more preferably from about 1.25 mm to about 1.75 mm.

One embodiment of an absorbent material of the present invention is particularly well suited for use in feminine hygiene products (See FIG. 2). Such a material has a basis weight of from about 100 g/m$^2$ to about 250 g/m$^2$ and a density between about 0.25 g/cc and 0.5 g/cc. More preferably, the density is from about 0.3 g/cc to about 0.45 g/cc and, most preferably about 0.4 g/cc.

In one embodiment, a material for use in a feminine hygiene product is air-laid as three strata: a bottom layer of pulp (without superabsorbent) with a basis weight of about 25 g/m$^2$; a middle layer with a basis weight of about 150 g/m$^2$ and which contains from about 10 g/m$^2$ to about 30 g/m$^2$ superabsorbent and from about 120 g/m$^2$ to about 140 g/m$^2$ pulp; and a top layer of pulp (without superabsorbent) with a basis weight of about 25 g/m$^2$. Relative to the total basis weight of the material, the level of superabsorbent ranges from about 5 to about 15 weight percent (g/m$^2$ of superabsorbent per g/m$^2$ material). Preferably, the level of superabsorbent is from about 7.5 weight percent to about 12.5 weight percent of the material. Most preferably, the material contains about 10 weight percent of superabsorbent. Thus, the middle layer of the material preferably contains from about 15 g/m$^2$ to about 25 g/m$^2$ superabsorbent and from about 125 g/m$^2$ to about 135 g/m$^2$ pulp and, more preferably about 20 g/m$^2$ superabsorbent and about 130 g/m$^2$ pulp. The middle layer containing pulp and superabsorbent can be laid down as a homogeneous blend or as a heterogeneous blend wherein the level of superabsorbent varies with proximity to the bottom layer.

In another embodiment, the material is air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 g/m$^2$ superabsorbent and from about 40 g/m$^2$ to about 65 g/m$^2$ pulp. When it is desired to keep absorbed fluid away from the top of the feminine hygiene product (i.e., away from the surface of the article in closest proximity to the wearer) the amount of superabsorbent in the first and second middle layers is adjusted such that there is a higher level of superabsorbent in the second middle layer. The superabsorbent in the first and second middle layers can be the same or a different superabsorbent.

Another embodiment of an absorbent material of the present invention is particularly well suited for use in diapers and incontinence products (FIG. 3). Because such articles are expected to absorb and retain larger quantities of less viscous fluid than a feminine hygiene article, such a material is heavier and, thus, has a preferred basis weight of from about 350 g/m$^2$ to about 450 g/m$^2$. The density of that material is between about 0.3 g/cc and 0.5 g/cc. More preferably, the density is from about 0.25 g/cc to about 0.45 g/cc and, most preferably about 0.4 g/cc.

In a manner similar to that described above, a material suitable for use in diapers can be air-laid as two, three or four strata. When three strata are used, a bottom layer has a basis weight of about 50 g/m$^2$; a middle layer has a basis weight of about 300 g/m$^2$ and contains from about 40 g/m$^2$ to about 200 g/m$^2$ superabsorbent and from about 100 g/m$^2$ to about 260 g/m$^2$ pulp; and a top layer has a basis weight of about 50 g/m$^2$. Preferably, the middle layer contains from about 70 g/m$^2$ to about 170 g/m$^2$ superabsorbent and from about 130 g/m$^2$ to about 230 g/m$^2$ pulp. Even more preferably, the middle layer contains about 80 g/m$^2$ superabsorbent and about 220 g/m$^2$ pulp or about 160 g/m$^2$ superabsorbent and about 140 g/m$^2$ pulp. The middle layer containing pulp and superabsorbent can be laid down as a homogeneous blend or as a heterogeneous blend wherein the level of superabsorbent varies with proximity to the bottom layer.

In a four strata embodiment, the middle layer is replaced with a first and second middle layer oriented as set forth above. Each of the first and second middle layers independently contains from about 20 g/m$^2$ to about 100 g/m$^2$ superabsorbent and from about 50 g/m$^2$ to about 130 g/m$^2$ pulp. In a preferred embodiment, the second middle layer has a higher level of superabsorbent than the first middle layer. In this way, the formed absorbent material has a tendency to keep absorbed fluid away from the body surface of the wearer of the article. The superabsorbent in the first and second middle layers can be the same or a different material.

An absorbent material for the present invention can be incorporate into an absorbent as a single or multiple-ply structure. Means of forming multiple-ply structures using folding are well known in the art. By way of example, a person skilled in art can "C", "G" or "Z" fold the absorbent material of the present invention prior to incorporating it into an absorbent article.

The following Examples illustrate preferred embodiments of the present invention and are not limiting of the specification and claims in any way.

EXAMPLE 1

A 400 g/m$^2$ absorbent material was produced in accordance with the above procedure using cold caustic extracted pulp. Overall composition of the web was 60% pulp and 40% Stockhausen T5318 superabsorbent material. The Gurley stiffness values of the absorbent material as well as absorbent cores from commercially available diapers were measured using a Gurley Stiffness Tester (Model No. 4171E), manufactured by Gurley Precision Instruments of Troy, N.Y. The instrument measures the externally applied moment required to produce a given deflection of a test strip of specific dimensions fixed at one end and having a concentrated load applied to the other end. Those commercial core materials were densified to achieve a range of densities comparable to the material of the present invention. The results are obtained in "Gurley Stiffness" values in units of milligrams. It should be noted that the higher the stiffness of the material, the less flexible and hence the less soft it is. Table 1 presents results of this test.

TABLE 1

Effect of Density On Gurley Stiffness

| | | | | | |
|---|---|---|---|---|---|
| Absorbent Mat'l. | Stiffness(mg) | — | 1021 | 1175 | 1575 |
| | Density (g/cc) | — | 0.34 | 0.43 | 0.5 |
| | Ratio(stiffn/den) | | 3303 | 2732 | 3150 |
| Huggies Ultratrim Med. Diaper | Stiffness(mg) | 1006 | 1313 | 2450 | 3775 |
| | Density (g/cc) | .027 | 0.31 | 0.4 | 0.51 |
| | Ratio(stiffn/den) | 3726 | 4235 | 6125 | 7401 |
| Pampers Baby Dry Stretch Med. Diaper | Stiffness(mg) | 1188 | 1638 | 2350 | 4400 |
| | Density (g/cc) | 0.267 | 0.3 | 0.42 | 0.51 |
| | Ratio (stiffn/den) | 4449 | 5460 | 5595 | 8607 |

EXAMPLE 2

Figure 4:
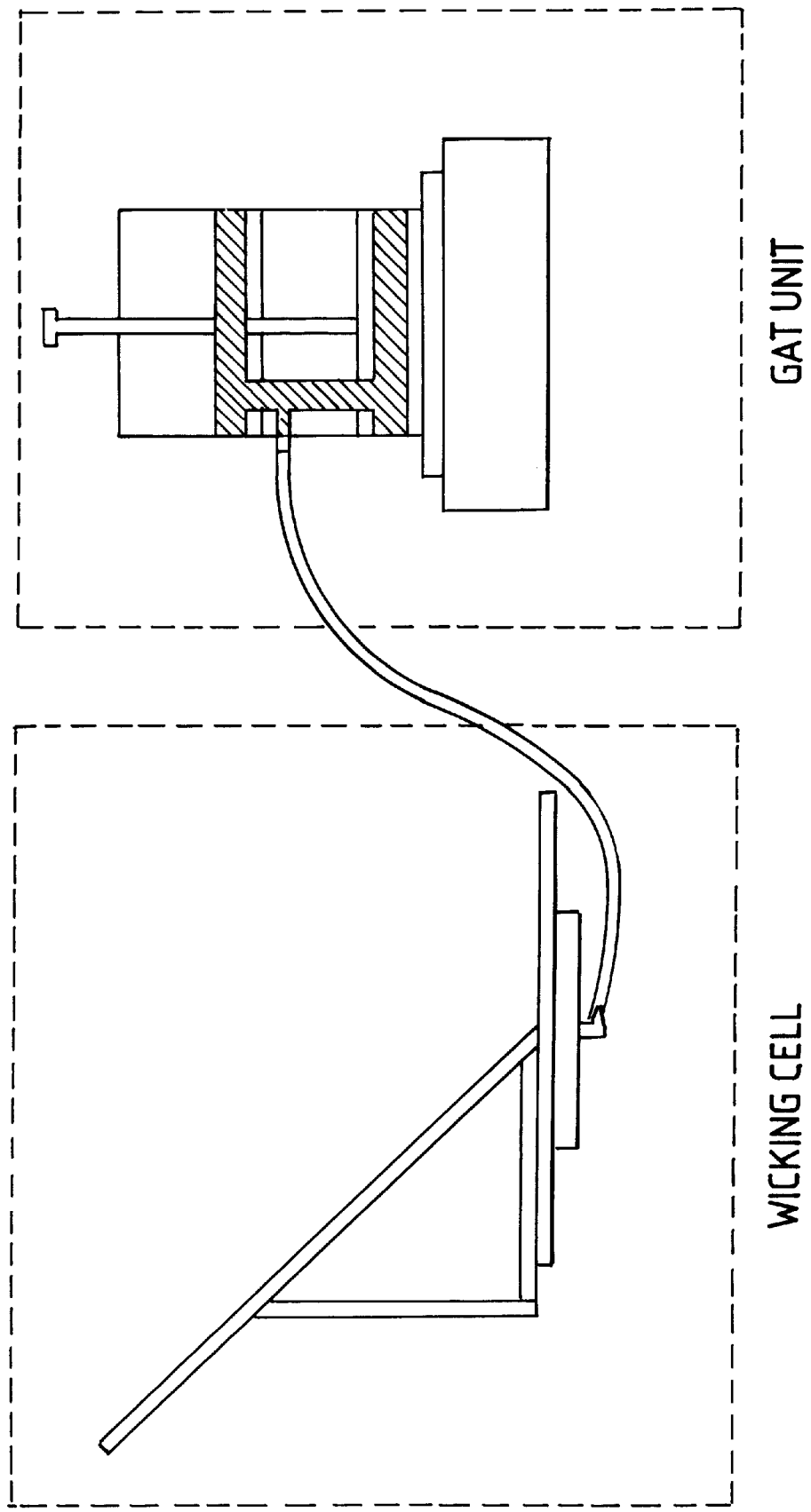
FIG. 4 is a schematic illustration of a device for measuring the wicking properties of absorbent material.

Absorbent materials of the present invention were made with basis weights of 400 g/m$^2$ and 600 g/m$^2$ containing 20 and 40 weight percent superabsorbent material, respectively. Wicking properties of the material and a core from a Huggies® diaper were measured using GATS system manufactured by M/K Systems of Danvers, Mass. FIG. 4 illustrates set up of the test. A 45° wicking test cell is attached to the absorption measurement device. The test cell essentially consists of a circular fluid supply unit for the test sample and 45° ramps. The fluid supply unit has a rectangular trough and liquid level is maintained at the constant height by the measuring unit. The test having dimension of 1"×12" was prepared. The sample was marked every inch along the length of the sample. The sample was then placed on the ramp of the test cell ensuring that one of the edges of the sample dips into the trough. The test was conducted for thirty minutes. Sample was removed after the specified period and cut along the marked distances. The cut pieces were placed into pre-weighed aluminum weighing dishes. The weighing dish containing wet samples were weighed again and then oven dried to a constant weight. By conducting a proper mass balance on the data, absorbency of the sample was determined at every inch. The following Table 2 presents results of the test:

TABLE 2

| | Absorbency (g/g) | | |
|---|---|---|---|
| Wicked Distance (in) | 400/20 Mat'l. | 600/40 Mat'l. | Huggies Diaper Core |
| 2 | 19.4 | 18.9 | 19.4 |
| 3 | 16.6 | 17.2 | 16.3 |
| 4 | 15.3 | 15 | 12.4 |
| 5 | 12.2 | 11.9 | 4.9 |
| 6 | 7.7 | 7.9 | 0.3 |
| 7 | 1.7 | 1.0 | |
| 8 | 0.2 | | |

The data show that the absorbent web of the present invention has a capability of transporting large amounts of fluid very rapidly from the liquid source.

Additional studies were performed using a 400 g/m² basis weight, 0.40 g/cc density, 40 weight percent superabsorbent material of the present invention (C11, C12 and C13) and the absorbent cores from commercially available Huggies® and Pampers diapers®; and commercial roll goods from Merfin and Concert. The results of those studies are summarized below in Table 3.

cial diapers, Huggies Ultratrim and Pampers Baby-dry Stretch, containing approximately 40% by weight of superabsorbent material granules were carefully removed and placed in a 28-mesh (Tyler series) sieve. Additional sieves of 35-mesh and 150-mesh were attached to the first sieve forming a column of increasingly fine sieves. The column of sieves was capped on either end to prevent the loss of fiber

TABLE 3

| Distance (in) | C11 (15% SAP) | C12 (28% SAP) | C13 (42% SAP) | Huggies (36% SAP) | Pampers (43% SAP) | Merfin (40% SAP) | Concert (30% SAP) |
|---|---|---|---|---|---|---|---|
| 2 | 15.3* | 19.3 | 22.3 | 19.3 | 24.6 | 17.9 | 11.6 |
| 3 | 13.9 | 17.1 | 20.6 | 17.7 | 19.6 | 15.5 | 11.2 |
| 4 | 12.7 | 15.6 | 19.1 | 16.4 | 14.6 | 9.2 | 8.5 |
| 5 | 11.6 | 13.8 | 17.4 | 13.9 | 10.6 | 1.06 | 5.7 |
| 6 | 10.4 | 12.2 | 14.4 | 10.5 | 5.5 | 0.16 | 0.82 |
| 7 | 9.1 | 9.9 | 8.3 | 4.4 | 1.4 | 0.16 | 0.04 |
| 8 | 7.7 | 6.7 | 0.75 | 0.50 | 0.1 | 0.15 | 0.01 |
| 9 | 5.8 | 1.4 | 0.10 | 0.00 | 0.00 | 0.00 | 0.02 |
| 10 | 2.4 | 0.07 | 0.08 | 0.00 | 0.00 | 0.00 | 0.00 |
| 11 | 0.07 | 0.07 | 0.10 | 0.00 | 0.00 | 0.00 | 0.00 |
| 12 | 0.07 | 0.07 | 0.09 | 0.00 | 0.00 | 0.00 | 0.00 |

*g/g

The results show the superior wicking ability of an absorbent material of the present invention when compared to commercially available material. It can be seen that material of the present invention wicked substantial amounts of fluid at a distance greater than 7 inches. In contrast none of the commercially available material distributed fluid beyond that distance.

EXAMPLE 3

A series of samples was evaluated for the integrity of the absorbent core in a range of material density from about 0.20 g/cc to about 0.50 g/cc. The test is performed on an Instron Universal Testing Machine. Essentially, the test measures the load required to pierce through the test sample, as described in the PFI Method of 1981. A test sample having dimensions of 50×50 mm is clamped on the Instron with a suitable fastening device. A 20 mm diameter piston traveling at the rate of 50 mm/min punctures the stationary sample. The force required to puncture the sample is measured. The following Table 4 presents results of the test.

TABLE 4

Density vs. Core Integrity

| Absorbent Mat'l. | | | | | |
|---|---|---|---|---|---|
| | Pad Integrity (N) | — | 12.4 | 16.3 | 15.8 |
| | Density (g/cc) | 0.20 | 0.234 | 0.326 | 0.433 |
| | Ratio (integ/den) | — | 53 | 50 | 36.5 |
| Huggies Ultra-trim Med. Diaper | Pad Integrity(N) | 4.1 | 5.11 | 7.6 | 8.24 |
| | Density (g/cc) | 0.19 | 0.254 | 0.328 | 0.455 |
| | Ratio (integ/den) | 21.6 | 20.4 | 23.0 | 18.2 |
| Pampers Baby Dry Stretch Diaper | Pad Integrity (N) | 2.9 | 3.9 | 6.6 | 9.37 |
| | Density (g/cc) | 0.16 | 0.26 | 0.38 | 0.42 |
| | Ratio (integ/den) | 18.1 | 15.0 | 17.4 | 22.3 |

The above data clearly indicate the absorbent material produced by the above invention is stronger than the conventional absorbent cores in the commercial diapers.

EXAMPLE 4

An amount of loosely held superabsorbent material in various absorbent materials was determined by shaking the material in a Ro-Tap Sieve Shaker manufactured by W. S. Tyler Co., Cleveland Ohio. Absorbent cores from commerand/or superabsorbent material. The sieve column was placed in the shaker and agitated for 10 minutes. The amount of superabsorbent material granules shaken loose from the absorbent cores, "free superabsorbent material", was determined by combining the residue contained in each of the sieves and separating the cellulosic fiber from the superabsorbent material. Comparative data for a present absorbent material containing 40% superabsorbent material were obtained in a similar fashion. The material was formed as in Example 1.

Data in Table 5 show that the present absorbent materials retained 100% of the superabsorbent material granules while the commercial cores from the Huggies and Pampers products lost approximately 16.6% and 29.5% by weight of the total superabsorbent material contained in the core.

TABLE 5

Determination of Free superabsorbent material in Absorbent Cores

| Product | Total Core Weight | Superabsorbent Weight | Free Superabsorbent Material | % Free Superabsorbent Material |
|---|---|---|---|---|
| Huggies ® Ultratrims | 22.63 g | 9.05 g | 1.51 g | 16.6 |
| Pampers ® Baby-Dry Stretch | 20.10 g | 8.04 g | 2.37 g | 29.5 |
| Absorbent Material | 20.45 g | 8.18 g | 0.00 g | 0.0 |

EXAMPLE 5

Absorbent material produced as in Example 1 was calendered with smooth and engraved (patterned) rolls to achieve desired density. Absorption capacity of the material against various applied pressures was measured by placing a known weight on top of the absorbent material, the known weight representing a specific pressure against the absorbent material, then contacting the absorbent material with a standard (0.9%) saline solution and allowing the material to absorb fluid until an equilibrium condition is attained. The following Table 6 presents results of the test:

TABLE 6

Effect Of Embossing On Absorbent Capacity

| Calender Type | Basis Weight (g/m²) | Density (g/cm³) | Absorption Against Load (g/m²) 0.3 psi | 0.7 psi |
|---|---|---|---|---|
| Engraved | 352 | 0.36 | 5430 | 4394 |
| Smooth | 405 | 0.35 | 5871 | 4666 |
| Engraved | 546 | 0.34 | 7912 | 6364 |
| Smooth | 596 | 0.35 | 8169 | 6518 |

It is evident from the test data that absorbency of calendered material with the pattern rolls is lower than the material calendered by the smooth rolls. The pattern roll essentially embosses the material. The lower absorbency may be due to damage caused to the superabsorbent material particles or to the introduction of very highly densified areas into the material as a result of the embossing. Damage to superabsorbent material granules and creation of super-densified zones in the absorbent material can have a negative impact on absorbent capacity. Therefore, it is preferred to calendar the material with a smooth roll.

EXAMPLE 6

Figure 5:
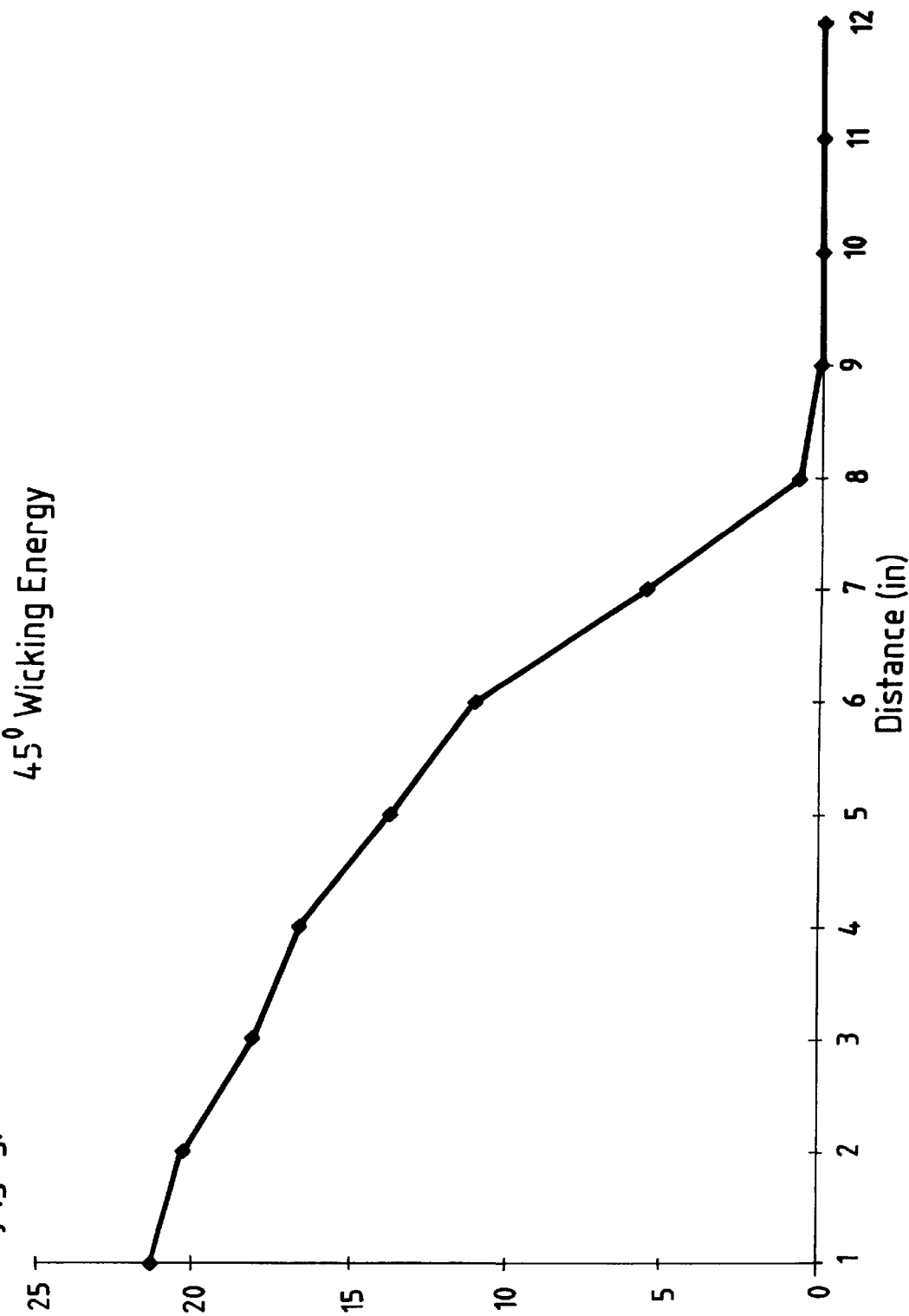
FIG. 5 is a representative plot of fluid absorption versus distance obtained in a 45° wicking test.

45 Degree wicking absorption was determined using the procedures of Example 2. The following groups of samples were tested: (a) absorptive material of the present invention with a basis weight of about 400 gm/m², a density of about 0.4 g/cc, and varying superabsorbent material contents of about 15 weight percent (Sample C11), 28 weight percent (C12), 39 weight percent (C1) or 42 weight percent (C13); (b) thermal bonded air-laid fluff obtained from Concert (Concert 500,280,130) or Merfin (44500); the absorbent core removed from a Huggies Diaper; and the absorbent core removed from a Pampers diaper. Samples C11, C12 and C13 were made using 100 percent cold caustic treated fibers. Sample C1 was made using a blend of 50 percent cold caustic treated fibers and 50 percent non-cold caustic treated fibers. For each sample, the amount of fluid absorbed per gram of sample was plotted against distance from the origin (source of fluid). A representative plot is shown in FIG. 5. The area under the curve was calculated using the following formula:

$$[(y_1)(x_2-x_1)+0.5(y_2-y_1)(x_2-x_1)+(y_2)(x_3-x_2)+0.5(y_3-y_2)(x_3-x_2)+ \ldots +(y_n)(x_n-x_{n-1})+0.5(y_n-y_{n-1})(x_n-x_{n-1})],$$

where $X_i$ is distance at the $i^{th}$ inch an $Y_i$ is absorbency at the $i^{th}$ inch.

This area was then multiplied by the gravitational constant (981 cm/s²) and the sine of 45° to result in the work value of ergs/g. The derived energy value was normalized for superabsorbent material by dividing by percent superabsorbent material (% SAP) content. The results of these studies are summarized below in Table 7.

TABLE 7

| Sample | % SAP | Total Wicking Energy (ergs/g) | Normalized Wicking Energy (ergs/g) | Density (g/cc) |
|---|---|---|---|---|
| C 1 | 39 | 161,299 | 4,136 | 0.38 |
| C 11 | 15 | 143,295 | 9,553 | 0.36 |
| C 12 | 28 | 152,509 | 5,447 | 0.36 |
| C 13 | 42 | 162,200 | 3,862 | 0.38 |
| Concert 500 | 45 | 93,016 | 2,067 | 0.12 |
| Concert 280 | 30 | 67,216 | 2,241 | 0.17 |
| Concert 130 | 18 | 56,219 | 3,123 | 0.13 |
| Merfin 44500 | 40 | 62,094 | 1,552 | 0.17 |
| Huggies | 36 | 133,889 | 3,719 | 0.15 |
| Pampers | 42 | 112,870 | 2,625 | 0.12 |

The data show that material of the present invention demonstrated superior wicking power when compared to the other materials.

EXAMPLE 7

Normalized Drying Power Energy

Various absorptive materials of the present invention, as well as commercially available absorptive materials (See Example 6 above), were examined to determine their ability to absorb fluids against a negative hydrostatic pressure gradient. The means used to determine this absorptive ability of the material (referred to herein as normalized drying power energy) were obtained using the well known drying power test (reference Burgeni et al., *Textile Research Journal*, 37 1967 362). Absorbency is measured under varying hydrostatic pressure heads (tension). Drying power energy is derived from the absorbency data.

Absorbency of the sample is measured at various negative hydrostatic pressures, i.e., negative hydrostatic heads. The negative hydrostatic pressure exerts a suction force on the sample. The absorbent material needs to have enough positive force to overcome the negative suction force in order to absorb fluid. The positive force results from the capillary pressure of the fiber matrix and osmotic pressure of the superabsorbent polymer. As the absorbent material picks up fluid, the positive pressure decreases. A point is reached when the positive force necessary to counter-balance the suction force insufficient. This point is referred to as equilibrium absorbency and represents the cessation of absorption. The hydrostatic pressure is systematically lowered in 5 cm increments from 35 cm to 1 cm of water, and the equilibrium absorbency at each hydrostatic tension value is measured. At a hydrostatic tension value of about 1 cm of water, the fiber network is completely saturated with the test fluid and the superabsorbent material polymer is fully hydrated. This point represents maximum absorption.

Figure 6:
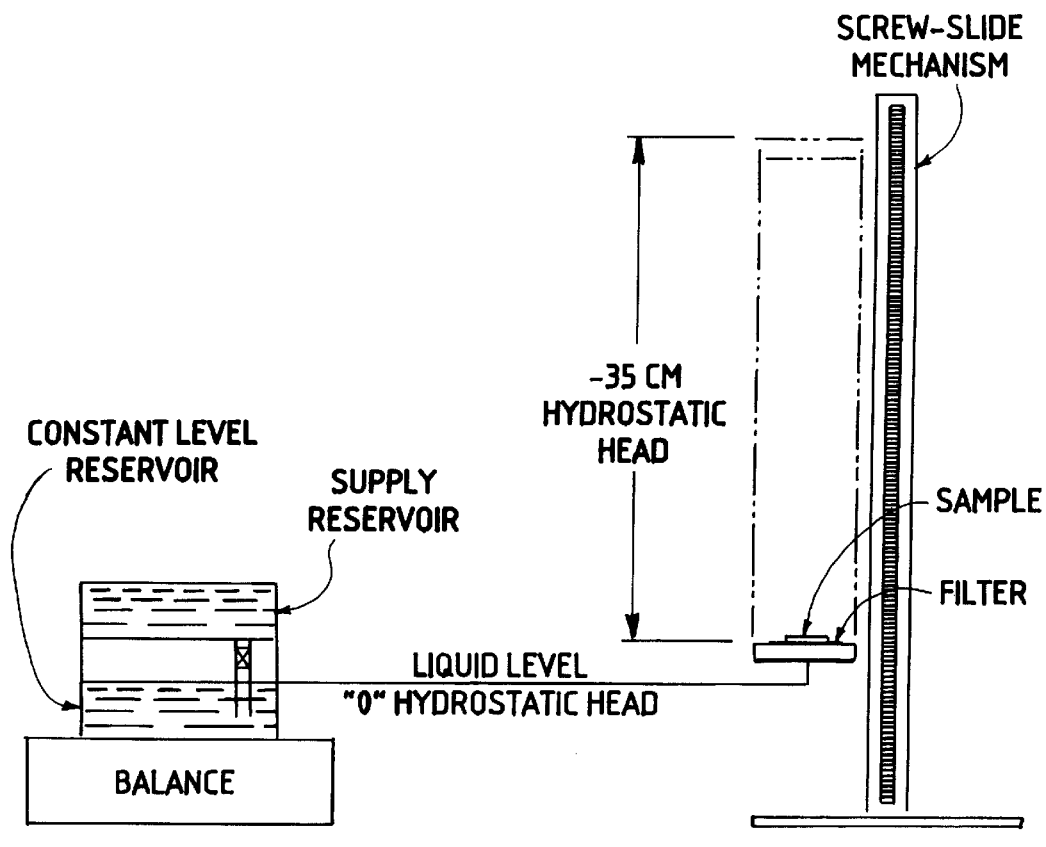
FIG. 6 is a schematic illustration of a device used to measure the drying power of absorbent materials.

A schematic illustration of an instrument used to obtain measurements for this characterization is shown in FIG. 6. As can be seen from FIG. 6, the instrument comprises a fluid source as well as an adjustable sample compartment. The fluid source comprises a constant-level fluid reservoir in conjunction with a supply reservoir. The entire fluid reservoir component is placed on a balance to allow for determination of the mass of the fluid lost or gained by the fluid reservoir. The fluid source is connected via a tube to the adjustable sample compartment. The adjustable multiport compartment (available from M-K Systems of Danvers, Mass.) comprises a solid support on which is placed a filter paper (Whatman #5) and a sample of absorbent material. The solid support mechanism together with the filter and sample are attached to a device which allows for raising and lowering of the sample height relative to the height of the fluid in the fluid reservoir. When the level of the sample and the sample compartment is the same as the level of the constant level fluid reservoir, there is 0 hydrostatic pressure head applied to the sample. As the sample level is raised above the level of fluid in the constant level reservoir, a negative hydrostatic pressure head is applied to the sample. The magnitude of the hydrostatic pressure head is equal to the difference in height between the sample and the fluid reservoir as measured in centimeters.

The various samples of absorptive material were placed in the instrument and fluid absorption measured over a range of hydrostatic pressures. The amount of fluid absorbed at each pressure (normalized for sample dry weight) was plotted against hydrostatic pressure. A representative plot is shown in FIG. 7. The area under the curve from point A to point Y is integrated. Drying power energy (ergs/g) is defined as this area. Normalized drying power energy is defined as the drying power energy value divided by the % superabsorbent material in the sample. The results of these studies are summarized below in Table 8.

TABLE 8

| Sample | % SAP | Total Drying Power Energy (ergs/g) | Normalized Drying Power Energy (ergs/g) | Density (g/cc) |
|---|---|---|---|---|
| C 1 | 39 | 283,622 | 7,272 | 0.38 |
| C 11 | 15 | 241,163 | 16,078 | 0.36 |
| C 12 | 28 | 276,103 | 9,861 | 0.36 |
| C 13 | 42 | 356,667 | 8,492 | 0.38 |
| Concert 500 | 45 | 105,345 | 2,341 | 0.12 |
| Concert 280 | 30 | 162,303 | 5,410 | 0.17 |
| Concert 130 | 18 | 141,592 | 7,866 | 0.13 |
| Merfin 44500 | 40 | 172,099 | 4,302 | 0.17 |
| Huggies | 36 | 161,686 | 4,491 | 0.15 |
| Pampers | 42 | 95,972 | 2,285 | 0.12 |

The data in Table 8 show that a material of the present invention has superior normalized drying power energy when compared to commercially available materials.

EXAMPLE 8

The samples used in Examples 6 and 7 were analyzed to determine their suppleness. Gurley stiffness measurements were obtained using the procedures of Example 1. The data from these studies are summarized below in Table 9.

TABLE 9

| | | Suppleness | |
|---|---|---|---|
| Sample | % SAP | Suppleness (g$^{-1}$) | Density (g/cc) |
| C 1 | 39 | 0.74 | 0.38 |
| C 11 | 15 | 0.792 | 0.36 |
| C 12 | 28 | 0.898 | 0.36 |
| C 13 | 42 | 1.235 | 0.38 |
| Concert 500 | 45 | 0.612 | 0.12 |
| Concert 280 | 30 | 1.429 | 0.17 |
| Merfin 44500 | 40 | 0.374 | 0.17 |
| Huggies | 36 | 0.890 | 0.15 |
| Pampers | 42 | 0.727 | 0.12 |

The data in Table 9 show that a high density material of the present invention has a suppleness comparable to that of low density commercially available samples.

EXAMPLE 9

Absorbent cores were carefully removed from Huggies® and Pampers® commercial diapers. The core was cut 35.88 cm long and 9.53 cm wide (14⅛ in×3¾ in). The absorbent cores were placed on 1.0 mil polyethylene and covered with a nonwoven cover (PGI Thermal Bonded Nonwoven Cover). In a similar fashion, a material of the present invention (basis wt. of 400 g/m², density of 0.40 g/cc, 40 weight percent superabsorbent material, a blend of cold caustic extracted and non-cold caustic extracted pulp) was placed on polyethylene and covered. All samples were tested for fluid acquisition and rewet using standard procedures well known in the art. These tests measure the rate of absorption of multiple fluid insults to an absorbent product or material and the amount of fluid that is rewet under 0.5 psi load. This method is suitable for all types of absorbent material, especially those intended for urine application.

Briefly, a fixed amount of saline solution is absorbed by an absorbent product or material. The absorption is recorded and a 30 minute absorption and wicking period follows. A filter paper and a 0.5 psi load is then applied to the test sample for 2 minutes. The fluid acquisition time and volume of rewet are recorded. This absorption and rewet process is repeated 3 times. Each value is reported along with the average and the standard deviation. This test measures rate of absorbency and absorption capacity. This test is performed in triplicate to verify results. For the present studies, 50 ml of saline were used as the fluid load. In addition to determining the acquisition times and rewet masses after the third insult, the wicking distance for each sample was calculated. The results of these studies are summarized below in Table 10.

TABLE 10

| | | | Acquisition and Rewet Test | | | |
|---|---|---|---|---|---|---|
| Sample | Core Weight (g) | Percent SAP | Third Acquisition Time (s) | Rewet (g) | Weight Difference | Wicking Length (cm) |
| Pampers | 19.504 | 43% | 86 | 2.246 | 25 | 15.24 |
| Huggies | 21.023 | 36% | 82 | 1.559 | 35 | 19.05 |
| Absorb. Mat'l | 15.602 | 37% | 47 | 0.63 | — | 27.31 |

It can be seen from the data in Table 10 that, despite a reduced sample weight, the material of the present invention showed a greater wicking length and a lower rewet value than commercially available materials.

What is claimed is:

1. An absorbent material having a basis weight of from about 100 g/m² to about 500 g/m², a density of from about 0.25 g/cc to about 0.50 g/cc, the material comprising a core including cellulosic fibers and a layer of tissue superimposed on an outer surface of the core, wherein at least some of the cellulosic fibers have been made by a process that includes the step of treating a liquid suspension of pulp at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes.

2. The material of claim 1 having a basis weight of from about 100 g/m² to about 250 g/m².

3. The material of claim 1 having a basis weight of from about 350 g/m² to about 450 g/m².

4. The material of claim 1 having a density of from about 0.30 to about 0.45 g/cc.

5. The material of claim 1 having a density of from about 0.35 to about 0.45 g/cc.

6. The material of claim 1 wherein at least 25 percent of the fibers are made by the process.

7. The material of claim 6 wherein at least 40 percent of the fibers are made by the process.

8. The material of claim 7 wherein at least 50 percent of the fibers are made by the process.

9. The material of claim 1 that contains from about 40 weight percent to about 100 weight percent cellulosic fibers and from about 0 weight percent to about 60 weight percent superabsorbent material.

10. The material of claim 9 that contains from about 10 to about 60 weight percent superabsorbent material.

11. The material of claim 10 that contains from about 20 to about 40 weight percent superabsorbent material.

12. The material of claim 10 that has normalized drying power energy of at least 6000 ergs/g.

13. The material of claim 12 that has normalized drying power energy of at least 7000 ergs/g.

14. The material of claim 13 that has normalized drying power energy of at least 8000 ergs/g.

15. The material of claim 14 that has normalized drying power energy of at least 9000 ergs/g.

16. The material of claim 15 that has normalized drying power energy of at least 10000 ergs/g.

17. The material of claim 10 that has normalized drying power energy of between about 6000 ergs/g and about 16000 ergs/g.

18. The material of claim 10 that has normalized wicking energy of at least 3000 ergs/g.

19. The material of claim 18 that has normalized wicking energy of at least 3500 ergs/g.

20. The material of claim 19 that has normalized wicking energy of at least 4000 ergs/g.

21. The material of claim 20 that has normalized wicking power energy of at least 5000 ergs/g.

22. The material of claim 21 that has normalized wicking energy of at least 7500 ergs/g.

23. The material of claim 10 that has normalized wicking energy of between about 3000 ergs/g and about 10000 ergs/g.

24. The material of claim 10 that has normalized drying power energy of at least 6000 ergs/g and a normalized wicking energy of at least about 3000 ergs/g.

25. The material of claim 24 that has normalized drying power energy of between about 6000 ergs/g and about 16000 ergs/g.

26. The material of claim 24 that has normalized wicking energy of between about 3000 ergs/g and about 10000 ergs/g.

27. The material of claim 10 that has a suppleness of greater than about 0.7 g$^{-1}$.

28. The material of claim 27 that has a suppleness of greater than about 0.8 g$^{-1}$.

29. The material of claim 28 that has a suppleness of greater than about 0.9 g$^{-1}$.

30. The material of claim 29 that has a suppleness of greater than about 1.0 g$^{-1}$.

31. The material of claim 10 having a suppleness of greater than about 0.7 g$^{-1}$, and a normalized drying power energy of greater than about 6000 ergs/g.

32. The material of claim 10 having a suppleness of greater than about 0.7 g$^{-1}$, and a normalized wicking energy of greater than about 3000 ergs/g.

33. The material of claim 10 having a suppleness of greater than about 0.7 g$^{-1}$, a normalized drying power energy of greater than about 6000 ergs/g and a wicking normalized energy greater than about 3000 ergs/g.

34. An absorbent article comprising the absorbent material of claim 1.

35. The article of claim 34 that is a diaper, a feminine hygiene product or an incontinence device.

36. The article of claim 34 wherein the absorbent material is folded into a multiple-ply structure.

37. The article of claim 34 wherein the absorbent material is folded into a multiple-ply structure.

38. An absorbent material having a density of from about 0.25 to about 0.5 g/cc and a suppleness of greater than about 0.7 g$^{-1}$, the material consisting essentially of:
   a) from about 40 weight percent to about 90 weight percent cellulosic fibers at least some of which fibers have been made by a process that includes the step of treating a liquid suspension of pulp at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes; and
   b) from about 10 weight percent to about 60 weight percent superabsorbent material.

39. The material of claim 38 further comprising a layer of tissue comprising from about 3 weight percent to about 20 weight percent of the absorbent material.

40. The material of claim 38 having a density of from about 0.30 to about 0.45 g/cc.

41. The material of claim 38 having a suppleness of greater than about 0.9 g$^{-1}$.

42. The material of claim 38 having a normalized drying power energy of greater than about 6000 ergs/g.

43. The material of claim 38 having a normalized wicking energy of greater than about 3000 ergs/g.

44. The material of claim 38 having a normalized drying power energy of greater than about 6000 ergs/g and a wicking energy of greater than about 3000 ergs/g.

45. An absorbent article comprising the absorbent material of claim 38.

46. The article claim 45 is a diaper, a feminine hygiene product or an incontinence device.

47. An absorbent material having a density of from about 0.25 g/cc to about 0.5 g/cc, a basis weight of from about 200 g/m² to about 500 g/m², a suppleness of greater than about 0.7 g$^{-1}$, a normalized drying power energy of greater than about 6000 ergs/g and a normalized wicking energy greater than about 3000 ergs/g, the material consisting essentially of:

a) from about 60 weight percent to about 80 weight percent cellulosic fibers at least some of which fibers have been made by a process that includes the step of treating a liquid suspension of pulp at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes;

b) from about 20 weight percent to about 40 weight percent superabsorbent material; and c) a layer of tissue comprising from about 3 weight percent to about 20 weight percent of the absorbent material.

48. An absorbent article comprising the absorbent material of claim 41.

49. The article of claim 48 that is a diaper, a feminine hygiene product or an incontinence device.

50. The article of claim 44 wherein the absorbent material is foled into a multiple-ply structure.

* * * * *